(12) United States Patent
Matsubara et al.

(10) Patent No.: US 11,857,163 B2
(45) Date of Patent: Jan. 2, 2024

(54) ENDOSCOPE HAVING SWINGING ELEVATOR

(71) Applicant: HOYA CORPORATION, Tokyo (JP)

(72) Inventors: Akiyoshi Matsubara, Saitama (JP); Tetsuya Tarumoto, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 31 days.

(21) Appl. No.: 17/719,884

(22) Filed: Apr. 13, 2022

(65) Prior Publication Data

US 2022/0257100 A1    Aug. 18, 2022

Related U.S. Application Data

(62) Division of application No. 16/308,714, filed as application No. PCT/JP2017/025235 on Jul. 11, 2017, now Pat. No. 11,395,581.

(30) Foreign Application Priority Data

Jul. 11, 2016 (JP) .................. 2016-137066
Jul. 11, 2016 (JP) .................. 2016-137067

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00098* (2013.01); *A61B 8/12* (2013.01); *G02B 23/24* (2013.01); *A61B 1/00131* (2013.01)

(58) Field of Classification Search
None
See application file for complete search history.

(56) References Cited

U.S. PATENT DOCUMENTS 9,089,263 B2    7/2015  Maruyama
2004/0082836 A1* 4/2004  Hino .................. A61B 1/00142
                                                     600/107
(Continued)

FOREIGN PATENT DOCUMENTS

CN        106061359 A      10/2016
DE    102016114881 A1 *  2/2018   ......... A61B 1/00071
(Continued)

OTHER PUBLICATIONS

International Search Report issued in International Bureau of WIPO Patent Application No. PCT/JP2017/025235, dated Aug. 15, 2017, along with an English translation thereof.

*Primary Examiner* — John P Leubecker
(74) *Attorney, Agent, or Firm* — GREENBLUM & BERNSTEIN, P.L.C.

(57) ABSTRACT

An endoscope includes a main body portion that has a housing recession portion that houses an elevator, a drive member arrangement space that houses a drive member and is closed off from the housing recession portion, a lid insertion space that puts the drive member arrangement space and an outer space into communication, and a lid member that can be inserted into the lid insertion space and liquid-tightly closes off the lid insertion space when inserted. Also provided is a fitting/holding member that is fitted to the lid member inserted into the lid insertion space and is fixed to the main body portion, wherein the lid member has a protruding portion, and the fitting/holding member can be inserted into the drive member arrangement space in a direction that is different from a protruding direction of the protruding portion of the lid member.

11 Claims, 8 Drawing Sheets

(51) Int. Cl.
    *A61B 8/12*          (2006.01)
    *G02B 23/24*       (2006.01)

(56)            References Cited

U.S. PATENT DOCUMENTS

| | | |
|---|---|---|
| 2016/0206180 A1 | 7/2016 | Hosogoe |
| 2016/0367114 A1 | 12/2016 | Iizuka |
| 2018/0035869 A1* | 2/2018 | Yamaya ............. A61B 1/00098 |
| 2018/0092512 A1 | 4/2018 | Hiraoka |
| 2018/0185045 A1 | 7/2018 | Ohki |
| 2019/0038114 A1 | 2/2019 | Hiraoka |

FOREIGN PATENT DOCUMENTS

| | | | | |
|---|---|---|---|---|
| EP | 3 097 843 A1 | | 11/2016 | |
| JP | 3527561 B2 | | 3/1996 | |
| JP | H11-4804 A | | 1/1999 | |
| JP | 11151202 A | * | 6/1999 | ......... A61B 1/00098 |
| JP | 2015-165839 A | | 9/2015 | |
| WO | 2016/021231 A1 | | 2/2016 | |

\* cited by examiner

ENDOSCOPE HAVING SWINGING ELEVATOR

CROSS-REFERENCE TO RELATED APPLICATION

The present application is a divisional of U.S. patent application Ser. No. 16/308,714, now U.S. Pat. No. 11,395,581, filed Dec. 10, 2018, which is a U.S. National Stage Application of International Patent Application No. PCT/JP2017/025235 filed Jul. 11, 2017, which claims the benefit of Japanese Patent Application Nos. 2016-137066, filed Jul. 11, 2016, and 2016-137067, filed Jul. 11, 2016. The disclosure of each of the above-noted applications is expressly incorporated herein by reference in its entirety.

TECHNICAL FIELD

The present invention relates to an endoscope, and in particular to an endoscope that includes an instrument elevating device for changing the protruding direction of an instrument protruding from a distal end of an insertion portion.

BACKGROUND ART

An instrument elevating device of an endoscope generally has an elevator that is axially supported at the distal end of an insertion portion, and the elevator is swung (rotated) by remote operations performed via a wire or the like from an operation portion. A housing recession portion for housing the elevator is formed in the main body portion at the distal end of the insertion portion. As an example of a configuration in which the elevator is axially supported, an endoscope is known in which shafts protrude from the two side faces of the elevator, a pair of shaft receiving holes are formed in the housing recession portion in order to support the two shafts, and the elevator is supported using the two shafts and the shaft receiving holes (Patent Document 1).

Also, instead of a structure in which an operation wire is directly connected to the elevator, this endoscope employs a structure in which a driving lever that rotates coaxially with the elevator is provided at the distal end of the insertion portion, and the operation wire is connected to the driving lever. The driving lever is arranged inside an elevator drive compartment, which is separated from the elevator housing portion by a partition wall, and an outer face opening portion of the elevator drive compartment is closed by a sealing lid. When closed with the lid, outside contaminant liquids and the like do not enter the elevator drive compartment, and it possible to prevent the driving lever and the operation wire from becoming soiled.

PRIOR ART DOCUMENT

Patent Document

Patent Document 1: JP 3527561B

SUMMARY OF INVENTION

Technical Problem

Whereas the functionality of endoscopes is improving, the diameter of the insertion portion is being reduced, and the layout of components at the distal end of the insertion portion has become increasingly dense. For this reason, there is desire for improvements in the efficient usage of space also in the configuration for axially supporting the elevator. For example, with a configuration such as that in Patent Document 1, shaft receiving portions are provided on the two sides of the elevator, and therefore the space usage efficiency is constrained on the two sides of the elevator, and there is a risk of an increase in the outer diameter of the distal end of the insertion portion if the component density increases. However, in the case of using a cantilevered axial support structure in which the elevator is axially supported on only one side in the axial direction in order to reduce the amount of space required for axial support, it is difficult to achieve sufficient support strength and stability.

Also, in the case of a structure in which the outer face opening portion of the elevator drive compartment is liquid-tightly closed with a lid as in the endoscope described above, there is known to be a configuration in which an adhesive is used to attach the lid to the main body portion that has the elevator drive compartment. The adhesive is applied to the peripheral edge of the lid, and the lid is then attached to the main body portion, and thus the lid and the main body portion (outer face opening portion) are liquid-tightly closed by the adhesive. With such a sealing structure that employs an adhesive, if the adhesive is applied unevenly, or if the adhesive degrades over time, there is a risk of degradation in liquid-tightness. This has caused problems in the manufacturing and maintenance of endoscopes.

An object of the present invention is to provide an endoscope that includes an elevator for changing the protruding direction of an instrument at the distal end of an insertion portion, and has a configuration in which the elevator is axially supported with favorable space usage efficiency in order to be able to contribute to a reduction in the diameter of the insertion portion, and can also simply and reliably obtain liquid-tightness for a drive mechanism that swings the elevator.

Solution to Problem

The following are aspects of an endoscope according to the present invention.

(1): An endoscope including an elevator that is provided at a distal end of an insertion portion and changes a protruding direction of an instrument by swinging, the endoscope including:

a main body portion that constitutes the distal end of the insertion portion;

a shaft member, an end portion of the shaft member on one side in a direction along an axis supporting the elevator so as to be capable of integrally rotating about the axis;

a drive member that is located at an intermediate position on the shaft member in the direction along the axis, and transmits, to the shaft member, operation force that is applied to an action point that is eccentric from the axis;

a first bearing that is provided between the end portion and a perpendicular line that extends along the axis from the action point, the first bearing supporting the shaft member so as to be capable of rotating about the axis relative to the main body portion; and a second bearing that is provided on a side opposite to the first bearing relative to the perpendicular line in the direction along the axis, the second bearing supporting the shaft member so as to be capable of rotating about the axis relative to the main body portion.

(2): An endoscope including:

an elevator configured to swing such that an instrument provided in an insertion portion of an endoscope changes a protruding direction;

a shaft member configured to rotate about an axis, the elevator being provided on an end portion of the shaft member on one side in an axial direction that extends along the axis, the shaft member supporting the elevator on one side in the axis direction, and the shaft member being configured to be capable of rotating integrally with the elevator about the axis;

a drive member that is fixed to the shaft member and is configured to input, to the shaft member, rotation force for rotation of the shaft member about the axis;

a first bearing and a second bearing that support the shaft member so as to be capable of rotating about the axis, on respective sides, with respect to a direction along the axis, of a position at which the shaft member is subjected to the rotation force.

(3): The endoscope described in section (2) above, wherein the endoscope further includes a main body portion that constitutes a distal end of the insertion portion, and the shaft member is inserted into a hole of the main body portion and is supported to the main body portion by the first bearing and the second bearing.

(4): The endoscope described in section (1) or (3) above, wherein the main body portion has a housing recession portion that houses the elevator, and the end portion of the shaft member protrudes from one of a pair of opposing walls of the housing recession portion, and another one of the pair of opposing walls is a substantially flat surface that opposes a leading end of the end portion.

(5): The endoscope described in any one of sections (1), (3), and (4) above, wherein the first bearing is constituted by a first circular cross-section portion that is provided in the shaft member and a first circular cross-section hole that is provided in the main body portion, the first circular cross-section portion being rotatably inserted into the first circular cross-section hole, and the second bearing is constituted by a second circular cross-section portion that is provided in the shaft member and a second circular cross-section hole that is provided in the main body portion, the second circular cross-section portion being rotatably inserted into the second circular cross-section hole.

(6): The endoscope described in section (5) above, further including an annular sealing member that liquid-tightly blocks a space between the first circular cross-section hole and the first circular cross-section portion.

(7): The endoscope described in section (5) or (6) above, wherein the main body portion includes a first member that has the first circular cross-section hole, and a second member that has the second circular cross-section hole, the first member includes an insertion space into which the second member can be inserted, and the second member is inserted into the insertion space in a liquid-tight manner, and when the second member is inserted, the first circular cross-section hole and the second circular cross-section hole are located at positions separated from each other along the axis.

(8): The endoscope described in any one of sections (5) to (7) above, wherein the shaft member includes a non-circular cross-section portion at a location between the first circular cross-section portion and the second circular cross-section portion in the direction along the axis, and the drive member includes a non-circular cross-section hole into which the non-circular cross-section portion is inserted.

(9): The endoscope described in section (1) or (3) above, wherein the main body portion has a drive member arrangement space that houses the drive member, and a lid insertion space that is in communication with the drive member arrangement space and receives insertion of a lid member for blocking the drive member arrangement space from a space outside the main body portion, and the second bearing is configured by a second circular cross-section hole provided in the lid member and a second circular cross-section portion provided in the shaft member.

(10): The endoscope described in section (1) or (3) above, wherein the main body portion has a circular cross-section hole that has an opening in a wall defining the drive member arrangement space and configures the first bearing when the shaft member is inserted, the shaft member has a second non-circular cross-section portion to which the drive member is connected, and an outer diameter at an end of the second non-circular cross-section portion on a side corresponding to the opening is greater than an inner diameter at the opening of the circular cross-section hole, such that movement of the shaft member toward the first bearing is restricted.

(11): The endoscope described in section (1) or (3) above, wherein the main body portion has a lid member for blocking the drive member arrangement space from a space outside the main body portion, the lid member includes a small diameter portion and a large diameter portion that have different outer diameters, and a step portion between the small diameter portion and the large diameter portion, the small diameter portion, the step portion, and the large diameter portion being arranged in order from a side corresponding to the drive member arrangement space, the main body portion has a small-diameter hole portion that comes into contact with the small diameter portion of the lid member, a large-diameter hole portion that comes into contact with the large diameter portion of the lid member, and a step face between the small-diameter hole portion and the large-diameter hole portion, and the lid member is configured such that movement of the lid member toward the drive member arrangement space in the axial direction is restricted due to the step portion of the lid member abutting against the step face.

(12): The endoscope described in section (10) above, wherein the main body portion has a lid member for blocking the drive member arrangement space from a space outside the main body portion, the lid member includes a small diameter portion and a large diameter portion that have different outer diameters, and a step portion between the small diameter portion and the large diameter portion, the small diameter portion, the step portion, and the large diameter portion being arranged in order from a side corresponding to the drive member arrangement space, the main body portion has a small-diameter hole portion that comes into contact with the small diameter portion of the lid member, a large-diameter hole portion that comes into contact with the large diameter portion of the lid member, and a step face between the small-diameter hole portion and the large-diameter hole portion, and the second non-circular cross-section portion is arranged between an end face of the small diameter portion of the lid member and the opening of the circular cross-section hole when the step portion of the lid member abuts against the step face.

(13): The endoscope described in any one of sections (1) and (3) to (12) above, wherein the main body portion has a housing recession portion that houses the elevator, a drive member arrangement space that houses the drive member and is liquid-tightly closed off from the housing recession portion, a lid insertion space that puts the drive member arrangement space and an outer space into communication, and a lid member that can be inserted into the lid insertion space and liquid-tightly closes off the lid insertion space when inserted, and the endoscope further includes a fitting/holding member that is fitted to the lid member inserted into the lid insertion space and is fixed to the main body by a mechanical fixing mechanism, the fitting/holding member restricting separation of the lid member from the lid insertion space.

(14): An endoscope including an elevator that is provided at a distal end of an insertion portion and changes a protruding direction of an instrument by swinging, and a drive member that swings the elevator according to an operation from an operation portion, the endoscope including:

a main body portion that has a housing recession portion that houses the elevator, a drive member arrangement space that houses the drive member and is liquid-tightly closed off from the housing recession portion, a lid insertion space that puts the drive member arrangement space and an outer space into communication, and a lid member that can be inserted into the lid insertion space and liquid-tightly closes off the lid insertion space when inserted; and a fitting/holding member that is fitted to the lid member inserted into the lid insertion space and is fixed to the main body by a mechanical fixing mechanism, the fitting/holding member restricting separation of the lid member from the lid insertion space.

(15): The endoscope described in section (14) above, wherein the lid member has a protruding portion that protrudes from the lid insertion space into the drive member arrangement space, and the fitting/holding member can be inserted into the drive member arrangement space in a direction that is different from a protruding direction of the protruding portion of the lid member, the fitting/holding member being configured to be fitted to the protruding portion of the lid member when inserted.

(16): An endoscope including:

a main body portion that has a drive member arrangement space that houses a drive member that swings an elevator that is provided at a distal end of an insertion portion of the endoscope and changes a protruding direction of an instrument, a lid insertion space that puts the drive member arrangement space and an outer space surrounding the insertion portion into communication, and a lid member that can be inserted from the outside space into the lid insertion space, and liquid-tightly closes off the lid insertion space and closes off the drive member arrangement space from the outer space when inserted into the lid insertion space, the lid member being configured to have a protruding portion that protrudes from the lid insertion space into the drive member arrangement space; and a fitting/holding member that is inserted into the drive member arrangement space, and is fixed inside the drive member arrangement space by sandwiching, along with the lid member, a wall between the drive member arrangement space and an outer space outside the main body portion and being fitted to the protruding portion of the lid member, thus restricting separation of the lid member from the lid insertion space.

(17): The endoscope described in section (16) above, wherein the fitting/holding member can be inserted into the drive member arrangement space in a direction that transverses a protruding direction of the protruding portion of the lid member, the fitting/holding member being configured to be fitted to the protruding portion of the lid member when inserted.

(18): The endoscope described in any one of sections (14) to (17) above, wherein the protruding portion of the lid member has a substantially cylindrical outer circumferential surface, and includes a fitting groove that extends along a circumferential direction in the cylindrical outer circumferential surface, and the fitting/holding member includes a plate-shaped portion that is fitted to the fitting groove, the fitting/holding member being configured such that the plate-shaped portion abuts against an inner face that defines the drive member arrangement space and restricts movement of the lid member in a separation direction.

(19): The endoscope described in section (18) above, wherein a side face of the fitting groove is flush with an inner face that defines the drive member arrangement space and surrounds the protruding portion of the lid member.

(20): The endoscope described in section (18) or (19) above, wherein the protruding portion of the lid member includes a pair of the fitting grooves that have bottom faces that are substantially parallel with each other, and the plate-shaped portion of the fitting/holding member includes a fitting recession portion having inner faces that sandwich the bottom faces of the pair of fitting grooves.

(21): The endoscope described in any one of sections (14) to (20) above, wherein the drive member is connected by a wire to an operation mechanism provided in an operation portion of the endoscope, and a stay coil receives insertion of the wire and is arranged inside the insertion portion, and the fitting/holding member has a coil support hole that receives insertion of one end of the stay coil.

(22): The endoscope described in any one of sections (14) to (21) above, wherein the lid insertion space is defined by a cylindrical inner circumferential surface, the lid member has a cylindrical outer circumferential surface that opposes the inner circumferential surface that defines the lid insertion space, and the endoscope further includes an annular sealing member that liquid-tightly blocks a space between the inner circumferential surface that defines the lid insertion space and the outer circumferential surface of the lid member.

(23): The endoscope described in any one of sections (14) to (22) above,
wherein in a state where the lid member is held in the insertion space via the fitting/holding member, an outer face of the lid member is substantially flush with an outer face of the main body portion that surrounds the lid member.

(24): The endoscope described in any one of sections (14) to (23) above,
further including a shaft member that is configured to rotate about an axis, and that supports the elevator and is capable of rotating integrally with the elevator about the axis,
wherein in a state where the lid member is held in the insertion space via the fitting/holding member, the lid member forms a bearing that supports the shaft member so as to be capable of rotating about the axis.

(25): The endoscope described in section (24) above,
wherein the bearing is constituted by a circular cross-section portion provided at one end of the shaft member and a circular cross-section hole that is provided in the lid member, the circular cross-section portion being rotatably inserted into the circular cross-section hole.

(26): The endoscope described in section (24) or (25) above,
wherein the shaft member includes a non-circular cross-section portion at a different location from the circular cross-section portion in the direction along the axis, and
the drive member includes a non-circular cross-section hole into which the non-circular cross-section portion is fitted.

(27): The endoscope described in any one of sections (14) to (16) above,
wherein the lid member includes a small diameter portion and a large diameter portion that have different outer diameters, and a step portion between the small diameter portion and the large diameter portion, the small diameter portion, the step portion, and the large diameter portion being arranged in order from a side corresponding to the drive member arrangement space,
the main body portion has a small-diameter hole portion that comes into contact with the small diameter portion of the lid member, a large-diameter hole portion that comes into contact with the large diameter portion of the lid member, and a step face between the small-diameter hole portion and the large-diameter hole portion, and
the lid member is configured such that movement of the shaft member in the axial direction of the shaft member is restricted due to the step portion of the lid member abutting against the step face.

Advantageous Effects of Invention

According to the endoscopes described above, the instrument elevator is axially supported with favorable space usage efficiency, thus making it possible to contribute to a reduction in the diameter of the insertion portion. Also, according to the endoscopes described above, it is possible to simply and reliably obtain liquid-tightness for the drive mechanism that swings the elevator.

DESCRIPTION OF EMBODIMENTS

Figure 1:
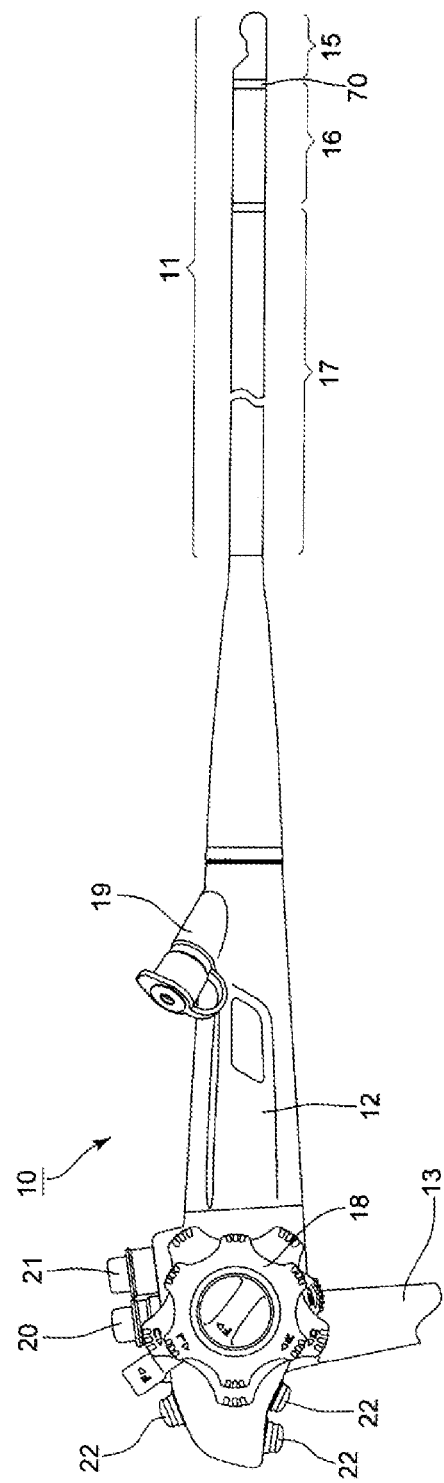
FIG. 1 is a diagram showing an example of an overall configuration of an ultrasonic endoscope in an embodiment of the present invention.
Figure 11:
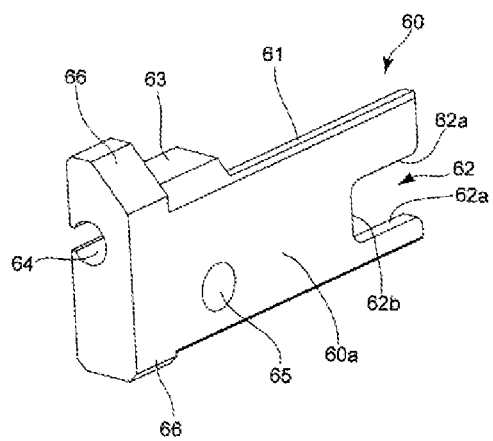
FIG. 11 is a perspective view of an example of a fitting/holding member of the ultrasonic endoscope in the embodiment of the present invention.
Figure 12:
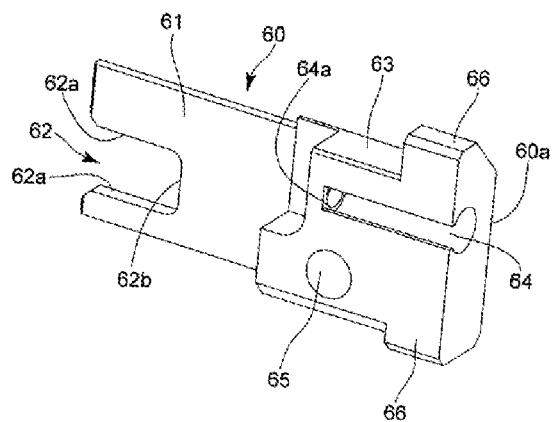
FIG. 12 is a perspective view of the example of the fitting/holding member of the ultrasonic endoscope in the embodiment of the present invention.
Figure 13:
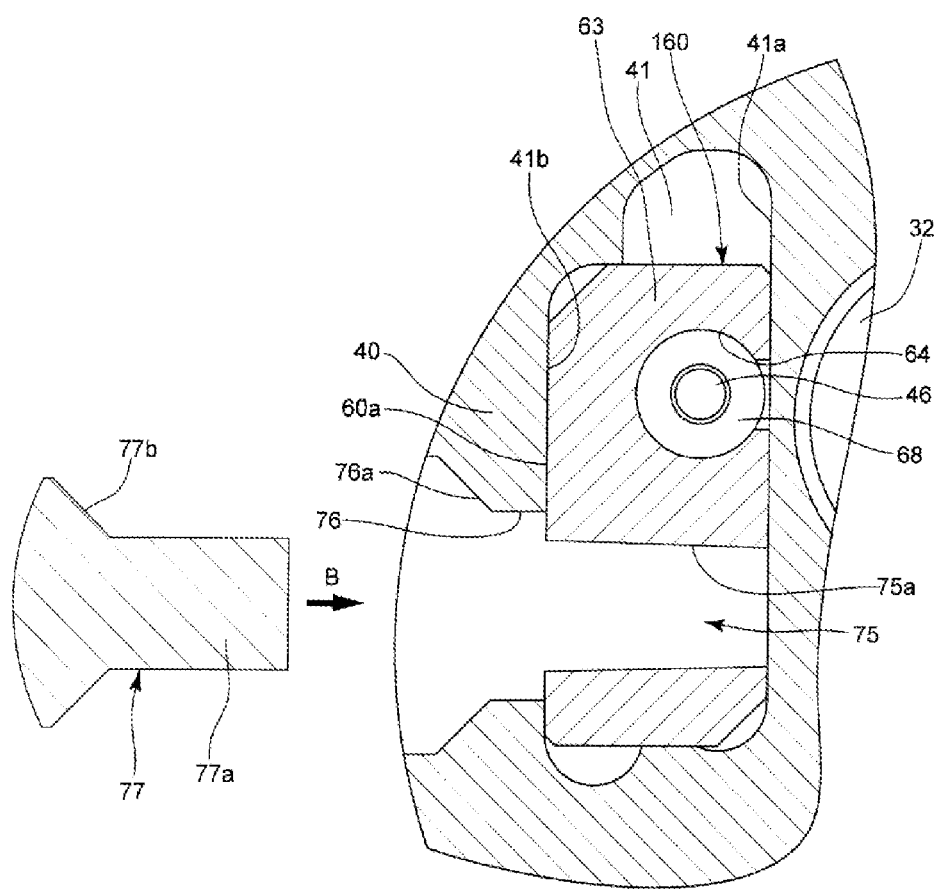
FIG. 13 is a cross-sectional view taken at a position similar to that in FIG. 8, and shows another aspect of a mechanical fixing mechanism for fixing the fitting/holding member shown in FIGS. 11 and 12.

Hereinafter, an endoscope according to an embodiment will be described with reference to the drawings. FIG. 1 shows the overall configuration of an ultrasonic endoscope 10 that is one embodiment. FIGS. 2 to 12 show the ultrasonic endoscope 10 according to a first embodiment, and FIG. 13 shows a second embodiment in which a portion of the configuration of the first embodiment has been modified.

As shown in FIG. 1, the ultrasonic endoscope 10 has a narrow-diameter insertion portion 11 for insertion into the body of a patient, an operation portion 12 that is connected to a base portion of the insertion portion 11, and a universal tube 13 that extends from the operation portion 12. The universal tube 13 is provided with a video connector and an ultrasonic signal connector that are not shown in the drawings, the video connector being for connection to a video processor (not shown), and the ultrasonic signal connector being for connection to an ultrasound observation device (not shown).

The insertion portion 11 is a portion for insertion into the patient's body, and has, in order from the forward side in the insertion direction, a distal end portion 15, a bending portion 16 that is bent by a remote operation from the operation portion 12, and a flexible tube 17 that is flexible. The operation portion 12 is provided with a curvature operation knob 18 for bending the bending portion 16, an instrument insertion opening 19 for insertion of a flexible wire-like instrument such as a puncture needle or forceps, a suction control valve 20 for performing suction in the distal end portion 15, an air/water feeding valve 21 for performing air/water feeding in the distal end portion 15, and multiple operation buttons 22 for inputting signals for performing image capture and the like.

Figure 2:
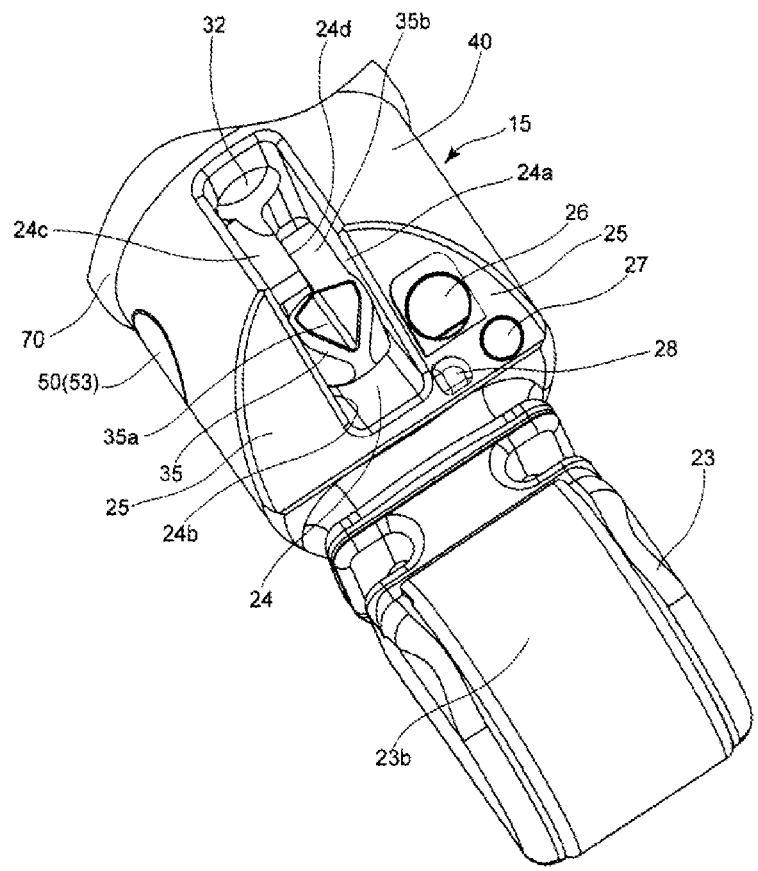
FIG. 2 is a perspective view of a distal end portion of an insertion portion of the ultrasonic endoscope in FIG. 1.
Figure 3:
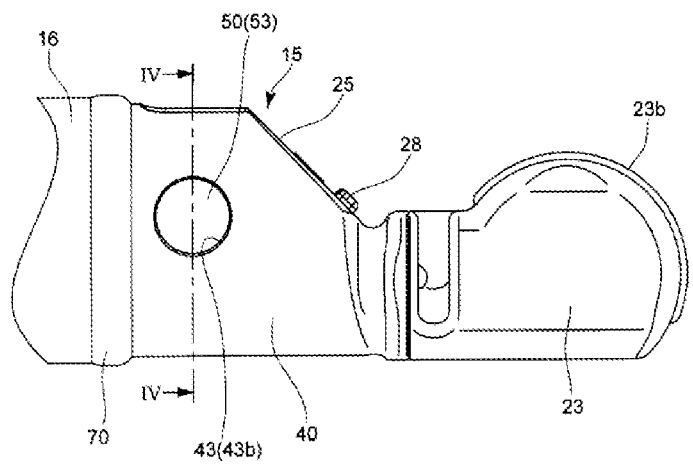
FIG. 3 is a side view of the distal end portion of the insertion portion of the ultrasonic endoscope.

As shown in FIGS. 2 and 3, an ultrasonic probe 23 is provided at the tip of the distal end portion 15 of the insertion portion 11. An ultrasonic signal cable 23a (see FIG. 6) is connected to the ultrasonic probe 23, is guided from the insertion portion 11 to the universal tube 13 via the operation portion 12, and is connected to an ultrasound observation device via the ultrasonic signal connector. The ultrasonic probe 23 has an acoustic lens 23b that has a curved convex surface, and when ultrasonic echography or treatment is performed, the acoustic lens 23b is brought into contact with a target site, ultrasonic waves are emitted, and an ultrasonogram is obtained.

As shown in FIG. 2, a housing recession portion 24 is provided rearward of the ultrasonic probe 23 in the distal end portion 15, and inclined end faces 25, which are inclined relative to the lengthwise direction of the insertion portion 11, are formed on respective sides of the housing recession portion 24. An objective window 26, an illumination window 27, and an air/water nozzle 28 are provided on one of the inclined end faces 25 of the housing recession portion 24. The lengthwise direction is the direction in which the insertion portion 11 shown in FIG. 1 extends from the flexible tube 17 toward the distal end portion 15, that is to say from left to right.

An objective lens constituting an observation optical system is provided in the objective window 26, and an image sensor unit 30 (see FIG. 4) is provided rearward of the observation optical system. The image sensor unit 30 is connected to an image signal cable (not shown). The illumination window 27 is connected to light guide fibers (not shown). The image signal cable and the light guide fibers are guided from the insertion portion 11 to the universal tube 13 via the operation portion 12, the image signal cable is connected to a video processor via the video connector, and the light guide fibers are connected to a light source apparatus that supplies illumination light. An image of an observation target is obtained via the objective window 26 and the observation optical system, and the image sensor unit performs photoelectric conversion on the obtained image to generate an image signal, and transmits the image signal to the video processor via the image signal cable. The video processor displays images on a monitor and/or records images. Illumination light emitted by the light source apparatus is guided by the light guide fibers and emitted from the illumination window 27.

The leading end of an air/water feeding tube 31 (see FIGS. 4 and 6), which is arranged inside the distal end portion 15, is connected to the air/water nozzle 28. The air/water feeding tube 31 branches into an air feeding tube and a water feeding tube inside the insertion portion 11, and the air feeding tube and the water feeding tube extend to the operation portion 12 and are connected to a cylinder that supports the air/water feeding valve 21. Tubes that extend from an air source and a water source are connected to the cylinder, and the air/water feeding valve 21 can be operated such that air is fed from the air source to the air/water nozzle 28 and water is fed from the water source to the air/water nozzle 28. The air/water nozzle 28 has an opening that faces the objective window 26 and the illumination window 27, and by feeding water and air to the air/water nozzle 28, it is possible to clean the objective window 26 and the illumination window 27 and remove foreign material that is affixed to the objective window 26 and the illumination window 27.

Figure 5A:
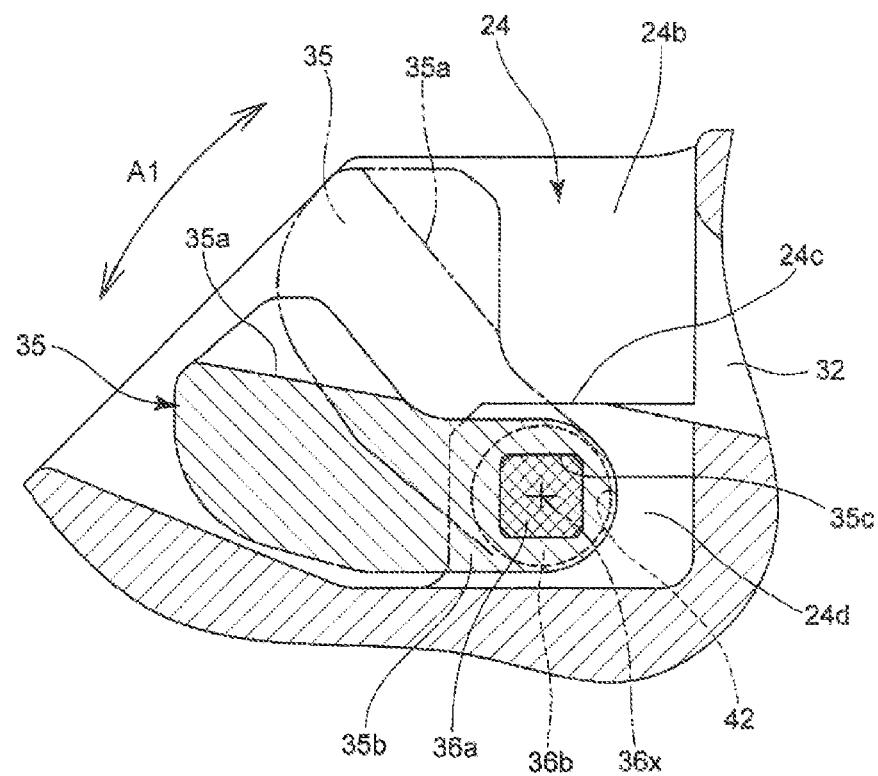
FIG. 5A is a cross-sectional view taken along line V-V in FIG. 4.

As shown in FIG. 2, the leading end of an instrument channel 32 is connected to a rear end portion of the housing recession portion 24. The instrument channel 32 extends to the operation portion 12 and is connected to the instrument insertion opening 19. When a flexible wire-like instrument (e.g., forceps, a puncture needle, or a contrast tube) is to be used, the flexible wire-like instrument is inserted into the instrument channel 32 through the instrument insertion opening 19, and protrudes from the housing recession portion 24. An elevator 35 is provided in the housing recession portion 24 and is capable of changing the protruding direction of the flexible wire-like instrument. A V-shaped support groove 35a is formed in the elevator 35, and this groove is deeper in the central portion than at the two sides in the width direction. As shown in FIG. 5A, the support groove 35a has a bottom face that is inclined relative to the lengthwise direction of the insertion portion 11, and when the flexible wire-like instrument is inserted through the instrument insertion opening 19 and reaches the housing recession portion 24, it is then supported by the support groove 35a, thus defining the direction of protrusion from the housing recession portion 24.

Figure 5B:
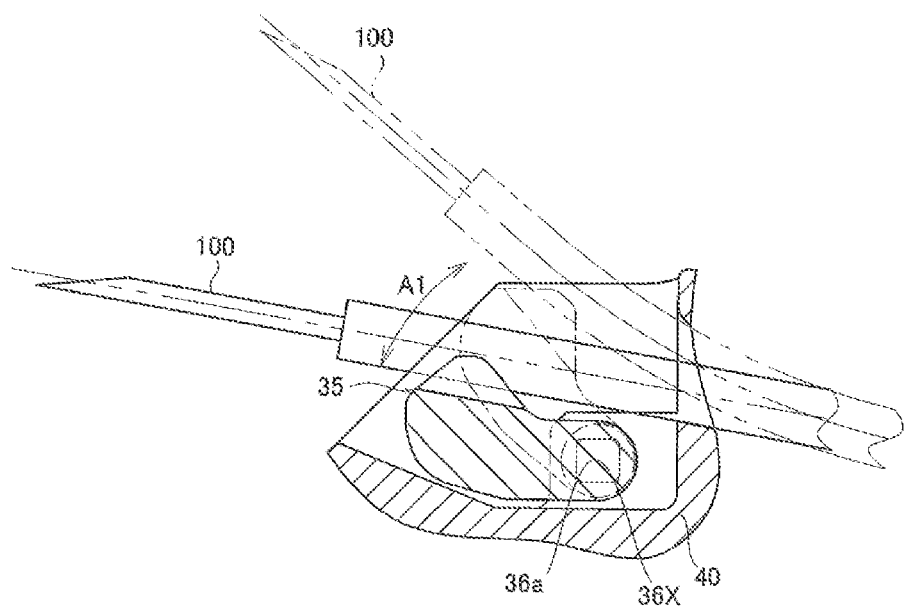
FIG. 5B is a diagram showing change in the protruding direction of forceps arranged on an elevator shown in FIG. 5A.

The elevator 35 is supported via a shaft member 36 supported inside the distal end portion 15, and is capable of swinging in a direction indicated by a double-headed arrow A1 in FIG. 5A. An axis 36x of the shaft member 36 extends in a direction that is substantially orthogonal to the ultrasonic scanning plane of the ultrasonic probe 23, and the axis 36x is the center of rotation when the elevator 35 swings. In FIG. 5A, the axis 36x extends in a direction perpendicular to the paper surface. In the state shown by solid lines in FIG. 5A, the elevator 35 is at an initial angle of being reclined on the bottom portion side of the housing recession portion 24, and the elevator 35 can be swung from this initial angle to a standing state shown by dashed double-dotted lines in FIG. 5A. FIG. 5B is a diagram showing change in the protruding direction of forceps 100 when the forceps 100 are placed on the elevator 35 as the instrument. The protruding direction of the forceps 100 is changed by swinging of the elevator 35 as shown in FIG. 5. The structure of the elevator 35 and members in the periphery thereof will be described in detail below.

The distal end portion 15 has a main body 40 that is made of a hard material. The main body 40 is called the main body portion along with a later-described lid member 50, and is also called a first member that constitutes the main body portion. The main body 40 has an approximately cylindrical outer face that is centered about an axis that extends in the lengthwise direction of the insertion portion 11, the ultrasonic probe 23 is connected to an end face of the cylindrical main body 40, and the inclined end faces 25 are formed at the boundary portions between the end face and the outer peripheral face of the main body 40.

Figure 4:
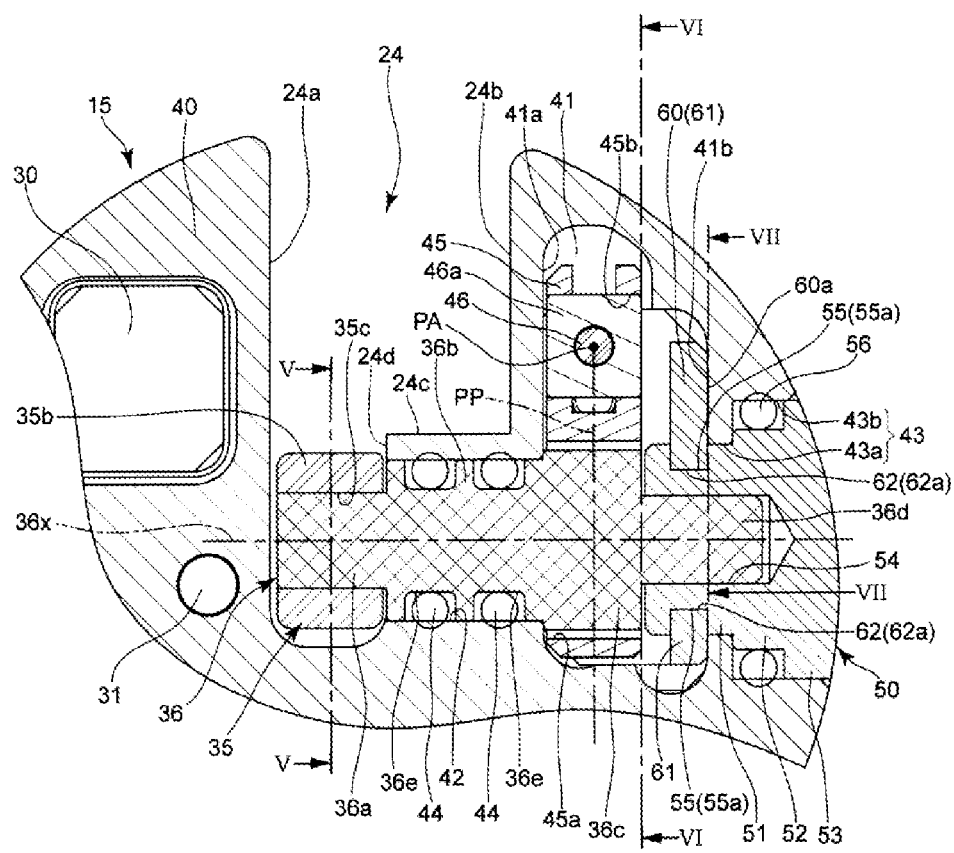
FIG. 4 is a cross-sectional view taken along line IV-IV in FIG. 3.

The housing recession portion 24 is formed as a groove-shaped portion that has a predetermined depth in the radial direction from the outer peripheral surface of the main body 40. As shown in FIG. 4, a first opposing wall 24a and a second opposing wall 24b, which are substantially parallel surfaces that oppose each other and are separated in a direction along the axis 36x of the shaft member 36, are formed inside the housing recession portion 24. As shown in FIG. 2, the front portion of the housing recession portion 24, that is to say the portion on the ultrasonic probe 23 side, has a substantially constant width, with the first opposing wall 24a and the second opposing wall 24b extending to the bottom portion, whereas a rearward portion of the housing recession portion 24 has a narrow portion at an intermediate position in the depth direction from the outer peripheral surface opening of the housing recession portion 24 toward the bottom portion. As shown in FIG. 4, the first opposing wall 24a has a flat shape extending from the outer peripheral surface of the main body 40 to the bottom portion of the housing recession portion 24, without a change in the shape of the wall surface even in the narrow portion. On the other hand, the second opposing wall 24b extends from the outer peripheral surface of the main body 40 to an intermediate position in the depth direction of the housing recession portion 24. A step portion 24c that extends in a direction of approaching the first opposing wall 24a is formed extending from the second opposing wall 24b at the intermediate position in the depth direction of the housing recession portion 24. Furthermore, a third opposing wall 24d that extends to the bottom portion of the housing recession portion 24 is formed extending from the step portion 24c. The third opposing wall 24d is flat and substantially parallel with the first opposing wall 24a and the second opposing wall 24b, and the constant-width narrow portion of the housing recession portion 24 is formed by the first opposing wall 24a and the third opposing wall 24d.

As shown in FIG. 4, a link housing space 41 is formed to one side of the housing recession portion 24 in the main body 40, and a shaft support hole 42 that puts the housing recession portion 24 and the link housing space 41 into communication with each other is formed so as to pass below the step portion 24d. The link housing space 41 is a space for disposing a link 45, which is a drive member for swinging the elevator 35. The shaft support hole 42 is a first circular cross-section hole that constitutes a first bearing of the shaft member 35. The link housing space 41 is a space that has a predetermined length along the lengthwise direction of the insertion portion 11 (see FIG. 6). As walls that define the link housing space 41, the main body 40 has a first support wall 41a that is located on the rear side of the second opposing wall 24b of the housing recession portion 24, and a second support wall 41b that opposes the first support wall 41a. The shaft support hole 42 has a circular cross-sectional shape with a substantially cylindrical inner circumferential surface, has one end opening that is formed in the third opposing wall 24d of the housing recession portion 24, and has another end opening that is formed in the first support wall 41a of the link housing space 41.

Furthermore, a lid insertion space 43 that puts the link housing space 41 and the outer space surrounding the insertion portion 11 (outer space) into communication is formed in the main body 40 so as to oppose the shaft support hole 42 across the link housing space 41. The lid insertion space 43 has a small-diameter hole portion 43a with a smaller opening diameter and a large-diameter hole portion 43b with a larger opening diameter, the small-diameter hole portion 43a has an opening in the second support wall 41b of the link housing space 41, and the large-diameter hole portion 43b has an opening in the outer peripheral surface of the main body 40. The small-diameter hole portion 43a and the large-diameter hole portion 43b are in communication with each other. The small-diameter hole portion 43a and the large-diameter hole portion 43b each have a cylindrical inner circumferential surface, and are arranged such that the central axes of the small-diameter hole portion 43a and the large-diameter hole portion 43b are coaxial with the central axis of the shaft support hole 42, which has a circular cross-section.

As shown in FIG. 4, the shaft member 36 has the axis 36x, and has a first non-circular cross-section portion 36a, a first circular cross-section portion 36b, a second non-circular cross-section portion 36c, and a second circular cross-section portion 36d, in this order from one end in a direction along the axis 36x. The first non-circular cross-section portion 36a forms an end portion that supports the elevator 35, the first circular cross-section portion 36b constitutes a first bearing along with the main body 40, and the second circular cross-section portion 36d constitutes a second bearing along with the main body 40. In other words, the shaft member 36 has the axis 36x, the elevator 35 is provided in an end portion on one side in the axial direction along the axis 36x, the elevator 35 is supported from one side in the axis 36x direction, and the shaft member 36 can rotate integrally with the elevator 35 about the axis 36x. In this structure, the elevator 35 is supported to the main body 40 by the shaft member 36, and is not supported thereto by any other member.

Figure 6:
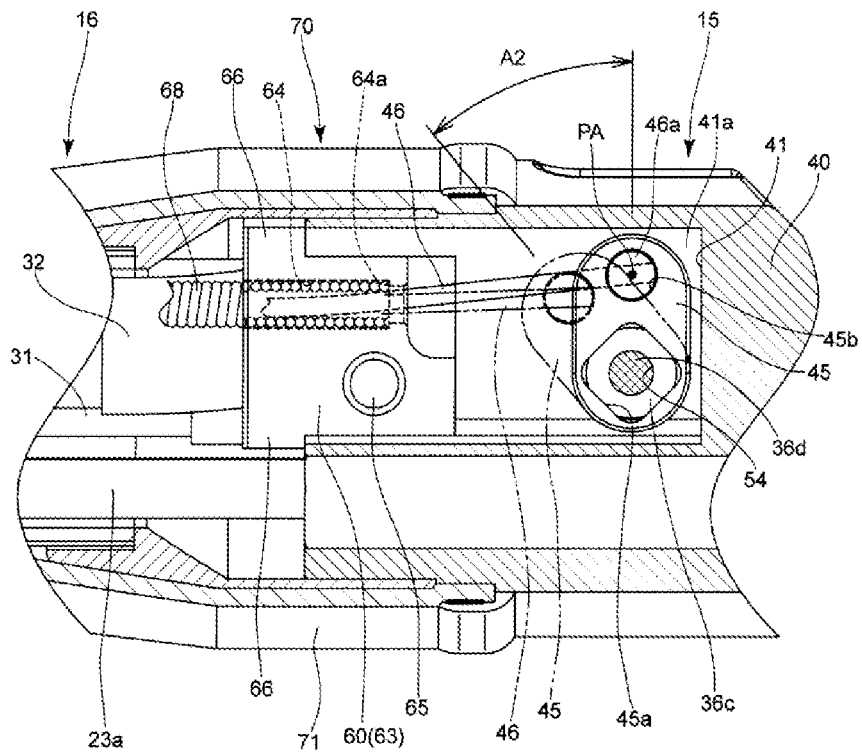
FIG. 6 is a cross-sectional view taken along line VI-VI in FIG. 4.

According to one embodiment, the first non-circular cross-section portion 36a and the second non-circular cross-section portion 36c each have a quadrangular cross-sectional shape with four sides surrounding the axis 36x as outer faces (see FIGS. 5 and 6). The first circular cross-section portion 36b and the second circular cross-section portion 36d each have a circular cross-sectional shape with a cylindrical surface centered about the axis 36x as the outer circumferential surface (see FIGS. 5 and 6). According to one embodiment, two annular grooves 36e, which are shaped as rings centered about the axis 36x, are provided in the outer surface of the first circular cross-section portion 36b (see FIG. 4).

The orientation of the shaft member 36 is defined such that the first non-circular cross-section portion 36a protrudes into the narrow portion that is sandwiched between the first opposing wall 24a and the third opposing wall 24d of the housing recession portion 24, and the first circular cross-section portion 36b is inserted into the shaft support hole 42 and supported in the main body 40. The outer diameter size of the first circular cross-section portion 36b and the inner diameter size of the shaft support holes 42 are approximately the same, and the first circular cross-section portion 36b is supported in the shaft support hole 42 so as to be capable of rotating about the axis 36x. An O ring 44 is supported in each of the two annular grooves 36e. The spaces between the first circular cross-section portion 36b and the shaft support hole 42 are closed in a liquid-tight manner by the compressed O rings 44, thus preventing liquids from intruding into the link housing space 41 through the housing recession portion 24. In other words, the O rings 44 are annular sealing members. Note that the O rings 44 are shown in an uncompressed and non-deformed initial state in FIG. 4.

As shown in FIG. 4, the elevator 35 has a narrow portion 35b that can be inserted into the narrow portion between the first opposing wall 24a and the third opposing wall 24d of the housing recession portion 24, and a shaft fitting hole 35c is formed in this narrow portion 35b. As shown in FIG. 5A, the shaft fitting hole 35c is a hole that has a quadrangular shape for fitting with the first non-circular cross-section portion 36a of the shaft member 36. Due to this fitting, the elevator 35 is prevented from rotating relative to the shaft member 36, and therefore rotates integrally with the shaft member 36 about the axis 36x. As shown in FIG. 4, the leading end of the first non-circular cross-section portion 36a does not protrude beyond the side face of the narrow portion 35b, and the leading end of the first non-circular cross-section portion 36a is substantially flush with the side face of the narrow portion 35b. For this reason, the first opposing wall 24a of the housing recession portion 24 can be made a substantially flat surface that does not have a hole or recession for insertion of the shaft member 36.

As shown in FIG. 4, the second non-circular cross-section portion 36c of the shaft member 36 is located inside the link housing space 41. The second non-circular cross-section portion 36c has a portion that is wider than the first circular cross-section portion 36b, and the position of the shaft member 36 in the direction along the axis 36x is determined by the side face of the second non-circular cross-section portion 36c abutting against the first support wall 41a of the link housing space 41. The shaft support hole 42 is a hole that has a circular cross-section and has an opening in the first support wall 41a. The outer diameter of the second non-circular cross-section portion 36c at the end on the open side is larger than the inner diameter at the opening of the shaft support hole 42. This therefore restricts movement of the shaft member 36 leftward of the arrangement position of the shaft member 36 shown in FIG. 4, that is to say restricts movement of the shaft member 36 to the first bearing side.

The link 45 is disposed inside the link housing space 41. The link 45 is a drive member for swinging the elevator. The link 45 is a drive member that is fixed to the shaft member 36, or more specifically is located at an intermediate position in the length direction of the shaft member 36 in the direction along the axis 36x, and transmits, to the shaft member 36, operation force that is applied to an action point that is eccentric from the axis 36x, and the link 45 is configured to input, to the shaft member 36, rotation force for rotation of the shaft member 36 about the axis 36x. As shown in FIG. 4, the link 45 is provided at a position extending along the first support wall 41a in the link housing space 41, and a gap is formed between the link 45 and the second support wall 41b.

As shown in FIG. 6, the link 45 has a shaft fitting hole 45a, which is a non-circular cross-section hole (e.g., a quadrangular hole) that fits with the second non-circular cross-section portion 36c of the shaft member 36, and due to this fitting, the link 45 is prevented from rotating relative to the shaft member 36, and therefore the link 45 rotates integrally with the shaft member 36 about the axis 36x. A wire end portion 46a provided at the leading end of the operation wire 46 is connected to a connection portion 45b provided at a position that is eccentric from the shaft fitting hole 45a of the link 45. The operation wire 46 extends from the insertion portion 11 to the operation portion 12, and can cause the operation wire 46 to become tense or loose by an operation performed on a tilting operation mechanism (not shown) provided in the operation portion 12.

As shown in FIG. 4, in the side portion of the second non-circular cross-section portion 36c of the shaft member 36, the side portion on the side opposite to the side in contact with the first support wall 41a is substantially flush with the side face of the link 45. The second circular cross-section portion 36d protrudes from this side face of the second non-circular cross-section portion 36c. The second circular cross-section portion 36d is in communication with the opening of the second support wall 41b of the link housing space 41, and is located in the lid insertion space 43.

Figure 9:
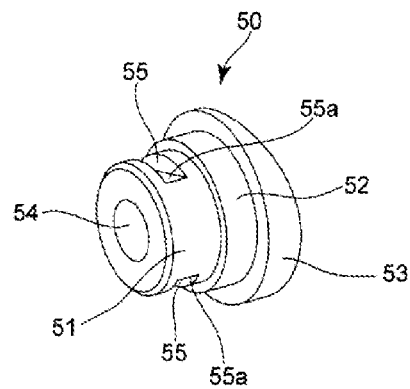
FIG. 9 is a perspective view of an example of a lid member of the ultrasonic endoscope in the embodiment of the present invention.
Figure 10:
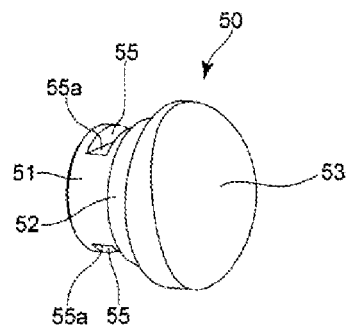
FIG. 10 is a perspective view of the example of the lid member of the ultrasonic endoscope in the embodiment of the present invention.

The lid member 50 is inserted into the lid insertion space 43 from the outer peripheral surface side of the main body 40. The lid member 50 is called the main body portion along with the main body 40, and the lid member 50 is also called a second member that constitutes the main body portion. The lid member 50 is made of a hard material, similarly to the main body 40. As shown in FIGS. 9 and 10, the lid member 50 is constituted by connecting a small diameter portion 51, a large diameter portion 52, and a head portion 53, each of which have a cylindrical outer circumferential surface, side-by-side and coaxially with each other, and the outer diameters of the small diameter portion 51, the large diameter portion 52, and the head portion 53 increase in this order. The small diameter portion 51 is configured to have a protruding portion that protrudes into the link housing space 41, which is in communication with the lid insertion space 43, when the lid member 50 is inserted into the lid insertion space 43. A shaft support hole 54 is formed in the lid member 50. The shaft support hole 54 is a second circular cross-section hole, and constitutes the second bearing along with the second circular cross-section portion 36d of the shaft member 36. The shaft support hole 54 is a hole that has a cylindrical inner circumferential surface, has one end opening in substantially the center of the end face of the small diameter portion 51, and has another end that is closed by the head portion 53. Two fitting grooves 55 that extend in the circumferential direction of the small diameter portion 51 are formed in the outer circumferential surface of the small diameter portion 51. The two fitting grooves 55 are at positions that are substantially symmetrical about the shaft support hole 54, and bottom faces 55a thereof are flat faces that are substantially parallel with each other (see FIGS. 4 and 7).

As shown in FIG. 4, the lid member 50 is inserted into the lid insertion space 43 beginning with the small diameter portion 51 side. The lid member 50 is inserted until the leading end of the large diameter portion 52 abuts against the step portion between the small-diameter hole portion 43a and the large-diameter hole portion 43b of the lid insertion space 43. When the lid member 50 is inserted in this way, the outer circumferential surface of the small diameter portion 51 is in contact with the inner circumferential surface of the small-diameter hole portion 43a of the lid insertion space 43, and the outer circumferential surface of the head portion 33 is in contact with the inner circumferential surface of the large-diameter hole portion 43b of the lid insertion space 43, thus restricting movement of the shaft member 36 in a direction orthogonal to the axis 36x of the shaft member 36. Also, the small diameter portion 51 of the inserted lid member 50 protrudes from the lid insertion space 43 into the link housing space 41, and the end face of the small diameter portion 51 is near the side face of the second non-circular cross-section portion 36c of the shaft member 36. Accordingly, the shaft member 36 and the lid member 50 are configured such that when the step portion between the large diameter portion 52 and the small diameter portion 51 of the lid member 50 abuts against the step face between the small-diameter hole portion 43a and the large-diameter hole portion 43b of the main body 40, the end face of the small diameter portion 51 is near the side wall of the second non-circular cross-section portion 36c, and the second non-circular cross-section portion 36c is arranged between the end face of the small diameter portion 51 and the opening of the shaft support hole 42 in the first support wall 41a. The term "near" refers to the case where, for example, the distance between the end face of the small diameter portion 51 and the end face of the second non-circular cross-section portion 36c is less than or equal to 0.1 mm. This suppresses rattling caused by movement in the direction along the axis 36x of the shaft member 36, thus making it possible for the elevator 35 to also swing without undergoing lateral movement.

Also, the step portion between the small diameter portion 51 and the large diameter portion 52 of the lid member 50 abuts against the step face between the small-diameter hole portion 43a and the large-diameter hole portion 43b, thus restricting movement of the lid member 50 in the direction of the axis 36x of the shaft member 36.

Furthermore, the two fitting grooves 55 provided in the small diameter portion 51 are located in the link housing space 41, and side faces of the fitting grooves 55 on one side are substantially flush with the second support wall 41b of the link housing space 41. As shown in FIGS. 2 and 4, the head portion 53 of the lid member 50 has an end face that is curved so as to be substantially flush with the outer circumferential surface of the main body 40 when the large diameter portion 52 of the lid member 50 is inserted into the lid insertion space 43. An O ring 56 is inserted, as an annular sealing member, between the outer circumferential surface of the large diameter portion 52 of the lid member 50 and the inner circumferential surface of the large-diameter hole portion 43b of the lid insertion space 43. The O ring 56 makes the space between the lid member 50 and the lid insertion space 43 liquid-tight, closes off the link housing space 41 from the space outside the lid insertion space 43, and prevents the intrusion of liquids into the link housing space 41 from the space outside of the lid insertion space 43.

The lid member 50 is attached to the main body 40 in the state where the shaft member 36 has been inserted into the shaft support hole 42 and the link housing space 41. At this time, the second circular cross-section portion 36d of the shaft member 36 is inserted into the shaft support hole 54 of the lid member 50 (see FIG. 4). The outer diameter size of the second circular cross-section portion 36d and the inner diameter size of the shaft support hole 54 are approximately the same, and the second circular cross-section portion 36d is supported in the shaft support hole 54 so as to be capable of rotating about the axis 36x. Also, the end face of the small diameter portion 51 of the lid member 50 opposes the side face of the second non-circular cross-section portion 36c of the shaft member 36, and movement of the shaft member 36 toward the lid insertion space 43 is restricted by the lid member 50.

The lid member 50 is fixed in and held in the link housing space 41 of the main body 40 by the fitting/holding member 60. As shown in FIGS. 11 and 12, the fitting/holding member 60 is elongated in one direction, and the fitting/holding member 60 is provided in the wall of the link housing space 41 such that the extended shape conforms to the lengthwise direction of the insertion portion 11. The fitting/holding member 60 has a plate-shaped portion 61 with a fitting recession portion 62 at a leading end, and a base portion 63 having a larger wall thickness than the plate-shaped portion 61. On one side of the fitting/holding member 60, side faces of the plate-shaped portion 61 and the side face of the base portion 63 are substantially flush and form a flat face 60a.

The fitting recession portion 62 has a pair of opposing faces 62a that are substantially parallel with each other, and a connection face 62b that connects the pair of opposing faces 62a. The base portion 63 is provided with, as a mechanical fixing mechanism, a coil support hole 64 that extends in the lengthwise direction of the fitting/holding member 60, and a threaded hole 65 that faces a direction along the thickness direction of the fitting/holding member 60. The wall surface of the coil support hole 64 is shaped as a cylindrical inner circumferential surface with an open portion on one lateral side, and the two ends of the coil support hole 64 are open. The inner diameter size of the opening on the front end side of the coil support hole 64 is set smaller, and an annular coil abutting face 64a that faces the interior of the coil support hole 64 is formed around this opening. The rear end of the base portion 63 has a wide shape with a pair of flanges 66 that protrude outward.

Figure 7:
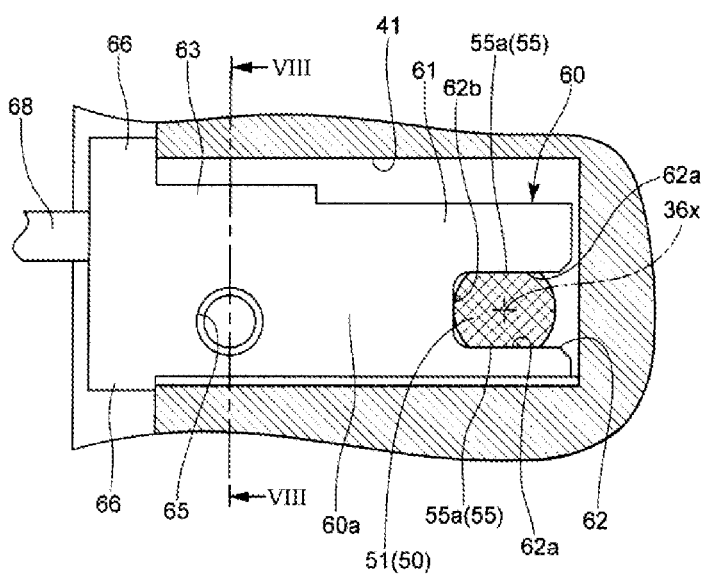
FIG. 7 is a cross-sectional view taken along line VII-VII in FIG. 4.

As shown in FIG. 7, the fitting/holding member 60 inserted into the link housing space 41 along the lengthwise direction of the insertion portion 11 such that the fitting recession portion 62 faces the leading end side, which is the ultrasonic probe 23 side (rightward in FIG. 7), that is to say from the bending portion 16 toward the distal end 15. More specifically, the fitting/holding member 60 is inserted into the portion between the link 45 and the second support wall 41b in the link housing space 41, while aligning the flat face 60a with the second support wall 41b. This insertion direction of the fitting/holding member 60 is a direction that is different from the protruding direction in which the small diameter portion 51, which protrudes into the link housing space 41, protrudes from the lid insertion space 43 of the lid member 50. According to one embodiment, it is preferable that, as shown in FIG. 7, this insertion direction is a direction that transverses the protruding direction of the protruding portion of the lid member 50. Also, according to one embodiment, it is preferable that it is a direction that is substantially orthogonal to the protruding direction of the small diameter portion 51. When the fitting/holding member 60 is inserted, the bottom faces 55a of the two fitting grooves 55 of the lid member 50 are sandwiched by the opposing faces 62a of the fitting recession portion 62 (see FIGS. 4 and 7), and the plate-shaped portion 61 is fitted into the fitting grooves 55. As shown in FIG. 4, the thickness of the plate-shaped portion 61 is substantially the same as the groove width of the fitting grooves 55. Accordingly, the plate-shaped portion 61 is fitted into the fitting grooves 55 without rattling. Also, due to the flat face 60a of the fitting/holding member 60 abutting against the second support wall 41b of the link housing space 41, movement of the fitting/holding member 60 toward the lid insertion space 43 is restricted (see FIG. 4). As a result, when fitted to the fitting/holding member 60, the lid member 50 is prevented from separating from the lid insertion space 43, and is fixed to the second support wall 41b in the link housing space 41 as shown in FIG. 4.

Figure 8:
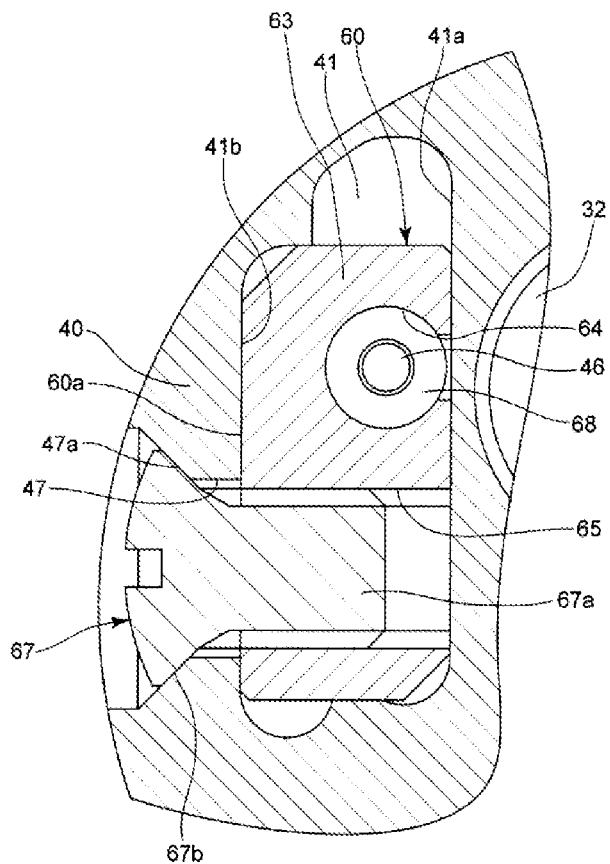
FIG. 8 is a cross-sectional view taken along line VIII-VIII in FIG. 7.

The position of insertion of the fitting/holding member 60 into the link housing space 41 is determined by the flange 66 abutting against the rear end portion of the main body 40 (see FIGS. 6 and 7). As shown in FIG. 8, a threaded passage hole 47, which is in communication with the threaded hole 65 of the fitting/holding member 60 in this state, is formed in the main body 40 as a mechanical fixing mechanism. A shaft portion 67a of a fixing screw 67, which is a mechanical fixing mechanism, is inserted into the threaded passage hole 47 and screwed into the threaded hole 65, thus fastening and fixing the fitting/holding member 60 to the main body 40. The opening portion of the threaded passage hole 47 is a countersink portion 47a, and the head portion of the fixing screw 67 has a conical surface 67b for abutting against the countersink portion 47a. In this configuration, when the fitting/holding member 60 is fixed as shown in FIG. 8, the head portion of the fixing screw 67 sinks into the threaded passage hole 47.

As shown in FIG. 6, the threaded hole 65 for screwing the fixing screw 67 is located inward of the connection portion 70 that connects the distal end portion 15 and the bending portion 16. In the connection portion 70, the outer side of the main body 40 is covered by a covering member 71 that is insulating. For this reason, when the ultrasonic endoscope 10 is in the completed state, the threaded passage hole 47 and the fixing screw 67 therein are not exposed to the outer surface of the insertion portion 11, and the liquid-tightness and insulation of the fixing portion achieved by the fixing screw 67 is kept by the covering member 71.

As shown in FIGS. 6 and 8, a stay coil 68 is inserted into the coil support hole 64 of the fitting/holding member 60.

The leading end of the stay coil 68 is arranged inside the insertion portion 11 while abutting against the coil abutting face 64a, and the operation wire 46 is inserted into the stay coil 68. The operation wire 46 passes through the inward opening portion of the coil abutting face 64a and extends to the forward side of the fitting/holding member 60, and the wire end portion 46a is connected to the connection portion 45b of the link 45. As previously described, the operation wire 46 extends from the insertion portion 11 to the operation portion 12, and is connected to a tilting operation mechanism (not shown) provided in the operation portion 12. The stay coil 68 supports the operation wire 46 so as to be capable of moving forward and rearward therein. According to this configuration, when the tilting operation means is operated, operation force is transmitted to the link 45 via the operation wire 46. Because the link housing space 41 has a liquid-tight structure, contaminants from the outside do not adhere to the link 45, the operation wire 46, the coil support hole 64, and the stay coil 68, and maintenance can be performed on the mechanism for driving the elevator 35 without trouble.

The distal end portion 15 is assembled as follows. The O rings 44 are inserted into the annular grooves 36e, and then the shaft member 36 is inserted through the lid insertion space 43 into the main body 40, with the first non-circular cross-section portion 36a on the leading side. At this stage, the elevator 35 is provisionally arranged inside the housing recession portion 24, the link 45 is provisionally arranged inside the link housing space 41, and the first non-circular cross-section portion 36a and the second non-circular cross-section portion 36c of the inserted shaft member 36 are respectively fitted into the shaft fitting hole 35c of the elevator 35 and the shaft fitting hole 45a of the link 45. Also, the first circular cross-section portion 36b of the shaft member 36 is rotatably supported in the shaft support hole 42 in the main body 40. Next, the O ring 56 is mounted to the outer side of the large diameter portion 52, the lid member 50 is inserted into the lid insertion space 43 with the small diameter portion 51 on the leading side, and the second circular cross-section portion 36d of the shaft member 36 is inserted into the shaft support hole 54 of the lid member 50, and thus the shaft member 36 is rotatably supported in the shaft support hole 54. After the lid member 50 is attached, the fitting/holding member 60 is then attached, and separation of the lid member 50 is prevented by the plate-shaped portion 61 fitting into the fitting grooves 55, and the fitting/holding member 60 is fixed with use of the fixing screw 67. When the fitting/holding member 60 is to be attached, the stay coil 68 is inserted into the coil support hole 64, and the operation wire 46, which has the wire end portion 46a that is connected to the connection portion 45b of the link 45, is inserted into the stay coil 68. Attaching the members in this way achieves a liquid-tight state in the link housing space 41 in which the intrusion of a liquid from the outside is prevented by the O rings 44 and the O ring 56, and contaminants do not adhere to the link 45 supported in the link housing space 41 and peripheral portions.

According to the structure described above, the shaft member 36 is supported to the main body 40 so as to be capable of rotating about the axis 36x, via the first bearing that is located between the narrow portion 35b of the elevator 35 and the link 45 and is constituted by the first circular cross-section portion 36b and the shaft support hole 42, and the second bearing that is located on the side opposite to the elevator 35 relative to the link 45 and is constituted by the second circular cross-section portion 36d and the shaft support hole 54. More specifically, the first bearing and the second bearing that axially support the shaft member 36 are provided on respective sides of a perpendicular line PP (see FIG. 4) that extends along the axis 36x from an action point PA (see FIGS. 4 and 6) at which operation force is applied when rotating the elevator 35. In other words, the first bearing and the second bearing rotatably support the shaft member 36 on respective sides, with respect to a direction along the axis 36x, of the position at which the shaft member 36 is subjected to rotation force.

As shown in FIG. 4, the first circular cross-section portion 36b, which constitutes the first bearing, has a larger diameter than the second circular cross-section portion 36d that constitutes the second bearing, thus making it possible to ensure rigidity while also having the two annular grooves 36e that support the O rings 44. Also, the second circular cross-section portion 36d that constitutes the second bearing is located at the end portion on the side opposite to the first non-circular cross-section portion 36a in the direction along the axis 36x, thus making it possible to reliably prevent inclination of the shaft member 36 and allow smooth rotation. Accordingly, it is possible to support the elevator 35 at one end of the shaft member 36, while also supporting the elevator 35 so as to be capable of rotating with high support strength and excellent stability.

Also, when the operation wire 46 connected to the action point PA location is made tense or loose, the link 45 moves (swings) within the range indicated by a double-headed arrow A2 in FIG. 6, and the elevator 35, which rotates integrally with the link 45 due to the shaft member 36, moves in conjunction. When the elevator 35 is at the initial angle indicated by solid lines in FIGS. 5A and 5B, the link 45 is at the location indicated by solid lines in FIG. 6. When the link 45 is pulled by the operation wire 46 and rotates to the position indicated by dashed double-dotted lines in FIG. 6, the elevator 35 rotates to the standing state indicated by dashed double-dotted line in FIGS. 5A and 5B. According to one embodiment, it is preferable that the rotation angle of the elevator 35 from the initial angle to the standing state (and the rotation angle of the link 45 that rotates along with the elevator 35) is approximately 40 degrees. When the operation wire 46 is no longer pulled, the elevator 35 and the link 45 both return to the initial angle.

As shown in FIG. 4, the elevator 35 is supported by the first non-circular cross-section portion 36a provided at one end of the shaft member 36, the elevator 35 is rotatably supported by the first bearing and the second bearing, and the support is concentrated on one side (the right side in FIG. 4) in the direction along the axis 36x relative to the narrow portion 35b of the elevator 35. For this reason, a structure for axial support, such as a shaft receiving hole, does not exist on the opposite side of the elevator 35 (the left side in FIG. 4), and the above embodiment is superior in terms of space usage efficiency on side of the elevator 35. Specifically, as shown in FIG. 4, the image sensor unit 30 and the air/water feeding tube 31 are arranged in the region to one side of the elevator 35 and the first non-circular cross-section portion 36a. Furthermore, although not shown, an illumination light guide cable (optical fiber bundle) for emitting light from the distal end portion 15 is also provided. Also, the ultrasonic signal cable 23a is provided below the recession portion 24 for housing the elevator 35, as shown in FIG. 6. For this reason, the arrangement positions of the image sensor unit 30, the air/water feeding tube 31, and the light guide cable are restricted so as to not increase the outer diameter of the distal end portion 15. If the shaft member 36 has an extending portion that extends leftward in FIG. 4 beyond the first non-circular cross-section portion 36a unlike the embodiment shown in FIG. 4, there is a risk that this extending portion of the shaft member 36, or a portion of the main body 40 that supports it, interferes with the image sensor unit 30 and the air/water feeding tube 31. If the positions of the image sensor unit 30 and the air/water feeding tube 31 are shifted in order to avoid interference, the outer diameter of the distal end portion 15 increases. In contrast, with the configuration of the embodiment shown in FIG. 4, the positions of the image sensor unit 30 and the air/water feeding tube 31 are not restricted, and the elevator 35 can be axially supported to the main body 40 so as to be capable of swinging via the shaft member 36, while also reducing the diameter of the distal end portion 15.

In the present embodiment, the shaft member 35 has a structure in which the elevator 36 is fixed at one end portion of the shaft member 35, and therefore rattling tends to easily occur when the elevator 36 swings, but the shaft member 35 is supported by two bearings, thus making it possible to prevent the occurrence of rattling. Moreover, the link 45 for transmitting action force or inputting rotation force is provided between the two bearings, thus making it possible to smoothly transmit action force or input rotation force with little rattling in the portion of the shaft member 35 that is subjected to the action force or rotation force.

The shaft member 35 is inserted into support holes of the main body 40 and the lid member 50 and supported to the main body 40 and the lid member 50 by the first bearing and the second bearing, and therefore the elevator 36 can be reliably swingably arranged at a predetermined position in the main body 40.

The shaft member 36 is configured so as to not protrude laterally from one side of the elevator 35, and therefore the first opposing wall 24a of the housing recession portion 24 that opposes the leading end of the first non-circular cross-section portion 36a can have a flat shape that does not have recessions/protrusions. Contaminants are not likely to adhere to this flat first opposing wall 24a when the ultrasonic endoscope 10 is used, and even if contaminants become adhered, cleaning can also be performed easily.

As described above, the shaft member 36 is rotatably supported by two bearings that are located on respective sides of the link 45 (perpendicular line PP), and therefore it is possible to achieve a configuration in which the elevator 35 is supported at one end of the shaft member 36, while also achieving superior support strength and support stability for the elevator 35.

The shaft support hole 42 and the shaft support hole 54 that constitute the two bearings are separately provided in the main body 40 and the lid member 50, and therefore by inserting the shaft member 36 and the lid member 50 into the main body 40 in this order, it is possible to easily assemble the structure in which the shaft member 36 is rotatably supported on two sides of the link 45 (perpendicular line PP). Furthermore, in the above embodiment, liquid-tightness in the link housing space 41 can be easily and reliably obtained by the O rings 44 and the O ring 56 that are attached to the outer sides of the shaft member 36 and the lid member 50, which are inserted into the main body 40 in order. The O rings 44 prevent outside liquids from flowing from the elevator 35 side toward the lid member 50 along the shaft member 36, thus making it possible to prevent the intrusion of liquids into the link housing space 41. The O ring 56 prevents outside liquids from flowing from the lid member 50 side toward the elevator 35 along the shaft member 36, thus making it possible to prevent the intrusion of liquids into the link housing space 41.

The link 45 includes the shaft fitting hole 45a, which is a non-circular cross-section hole for insertion of the second non-circular cross-section portion 36c of the shaft member 36, and therefore the link 45 can transmit operation force or input rotation force to the shaft member 36 without loss.

The second bearing is constituted by the lid member 50 that is provided at one end of the main body 40, and therefore the size of the distal end portion 15 can be reduced while also ensure sufficient housing space for arrangement of the link 45.

The outer diameter of the second non-circular cross-section portion 36c of the shaft member 36 at the end on the opening side that opposes the shaft support hole 42 is larger than the inner diameter of the opening of the shaft support hole 42, and therefore the second non-circular cross-section portion 36c of the shaft member 36 is prevented from moving to the side on the first bearing. For this reason, the elevator 35, which is fixed to the end of the shaft member 36, can be swung while preventing lateral movement along the axis 36x.

As shown in FIG. 4, when the step portion between the large diameter portion 52 and the small diameter portion 51 of the lid member 50 abuts against the step face between the small-diameter hole portion 43a and the large-diameter hole portion 43b of the main body 40, the second non-circular cross-section portion 36c is arranged between the end face of the small diameter portion 51 and the opening of the shaft support hole 42 in the first support wall 41a. In this configuration, the end face of the small diameter portion 51 is near the side wall of the second non-circular cross-section portion 36c. For this reason, the second non-circular cross-section portion 36c is prevented from moving toward the two sides in the axis 36x direction in the link housing space 41, and it is possible to swing the elevator 35 while preventing lateral movement toward the two sides in the axis 36x direction.

Also, by unscrewing the fitting/holding member 60, the lid member 50 and the shaft member 36 can be easily removed, and the ultrasonic endoscope 10 is superior in terms of ease of maintenance after production.

Also, the lid insertion space 43, which puts the link housing space 41 into communication with the outside, is closed in a liquid-tight manner with respect to the outside by the lid member 50 having the large diameter portion 52 to which the O ring 56 is attached, and separation of the lid member 50 from the lid insertion space 43 is prevented by the fitting/holding member 60 that is mechanically fitted to the lid member 50. The fitting/holding member 60 can be easily fixed to the main body 40 with use of the fixing screw 67. According to this configuration, liquid-tightness in the link housing space 41 can be obtained without depending on adhesion, and a decrease in liquid-tightness is not caused by the uneven application of an adhesive or degradation of the adhesive. Also, the lid member 50 for positioning the shaft member 36 in the main body 40 can be fixed to the main body 40 by the fitting/holding member 60, thus making it possible to easily remove the lid member 50 and the fitting/holding member 60 after assembly performed without adhesion, and superior ease of maintenance is achieved.

The fitting of the fitting/holding member 60 to the lid member 50 is achieved by the fitting/holding member 60 being inserted in a direction that is different from the protruding direction of the protruding portion of the lid member 50, which in one embodiment is a direction that transverses the protruding direction. In other words, the lid member 50 and the fitting/holding member 60 can each be easily attached to the main body 40.

The plate-shaped portion 61 of the fitting/holding member 60 is fitted into the fitting grooves 55 of the lid member 50 and abuts against the second support wall 41b of the link housing space 41, and therefore movement of the lid member 50 in the direction of separation can be easily prevented with a simple configuration. At this time, the side faces of the fitting grooves 55 are flush with the face of the second support wall 41b that surrounds the portion of the lid member 50 that protrudes into the link housing space 41, and therefore the fitting/holding member 60 can be reliably fixed to the second support wall 41b. Furthermore, the portion of the lid member 50 that protrudes into the link housing space 41 at this time has the pair of fitting grooves 55a that have bottom faces that are substantially parallel with each other, and the plate-shaped portion 61 of the fitting/holding member 60 has the fitting recession portion 62 that has inner surfaces that sandwich the bottom faces of the 55a of the fitting grooves 55, and therefore the fitting/holding member 60 can be easily fitted into the fitting grooves 55 by inserting the fitting/holding member 60 into the link housing space 41 along the second support wall 41b.

When the lid member 50 is held inside the link housing space 41 via the fitting/holding member 60, the outer surface of the lid member 50 is substantially flush with the outer surface of the main body 40 that surrounds the lid member 50, and therefore there are no recession portions where liquids can accumulate in this portion. This therefore prevents a situation in which a liquid accumulates in a recession portion and intrudes toward the link housing space 41 through a gap between the lid member 50 and the main body 40.

The fitting/holding member 60 holds the lid member 50, and by the stay coil 68 being inserted into the coil support hole 64, the fitting/holding member 60 also functions as a member for supporting and guiding the operation wire 46 in the link housing space 41. For this reason, there is no need to separately form a member for supporting and guiding the operation wire 46 in the link housing space 41, and the configuration can be simplified by reducing the number of components, and this further contributes to a reduction in the size of the distal end portion 15.

A fitting/holding member 160 according to an embodiment shown in FIG. 13 has a pin insertion hole 75 instead of the threaded hole 65 in the fitting/holding member 60 according to the embodiment shown in FIG. 8. The pin insertion hole 75 has a conical inner circumferential surface 75a according to which the inner diameter gradually decreases while extending from the side corresponding to the second support wall 41b of the link housing space 41 to the first support wall 41a side. With the exception of the pin insertion hole 75, the fitting/holding member 160 has the same configuration as the fitting/holding member 60, and is inserted into the link housing space 41 similarly to the fitting/holding member 60 shown in FIGS. 6 and 7. The main body 40 is provided with a pin passage hole 76 that is in communication with the pin insertion hole 75 of the fitting/holding member 160 when inserted into the link housing space 41.

A fixing pin 77 serving as a mechanical fixing mechanism is inserted into the pin passage hole 76 and the pin insertion hole 75 in the direction indicated by arrow B in FIG. 13. A shaft portion 77a of the fixing pin 77 has a cylindrical outer circumferential surface with a substantially constant outer diameter. At an intermediate position in the pin insertion hole 75 in the direction from the second support wall 41b side, which is the front side in the shaft portion 77a insertion direction, to the first support wall 41a side, which is the rear side, the inner diameter of the inner circumferential surface 75a becomes smaller than the outer diameter of the shaft portion 77a, and the shaft portion 77a of the fixing pin 77 is press-fitted into the pin insertion hole 75. The opening portion of the pin passage hole 76 is a countersink portion 76a, and the head portion of the fixing pin 77 has a conical surface 77b that corresponds to the shape of the countersink portion 76a. When the fixing pin 77 is inserted to a position at which the conical surface 77b abuts against the bottom face of the countersink portion 76a, the fixing pin 77 is prevented from moving relative to the main body 40. As a result, the fitting/holding member 160 is fastened and fixed to the main body 40 via the press-fitted fixing pin 77. When this fitting/holding member 160 is fixed, the head portion of the fixing pin 77 sinks into the pin passage hole 76 and does not protrude outward from the main body 40. Note that according to one embodiment, the outer circumferential surface of the shaft portion 77a of the fixing pin 77 may be preferably press-fitted into the pin insertion hole 75 even if instead of having a cylindrical shape with a substantially constant outer diameter, it has a conical shape with a taper angle that is smaller than the inner circumferential surface 75a of the pin insertion hole 75.

Although a description has been given above based on the illustrated embodiments, the present invention is not limited to these embodiments. For example, although the illustrated embodiments are applied to an ultrasonic endoscope, the present invention is also applicable to an endoscope other than an ultrasonic endoscope, as long as it has an elevator.

As previously described, from the view point of ease of assembly and disassembly, it is preferable that the shaft support hole 54 is provided in the lid member 50, which is separate from the main body 40, but according to one embodiment, a configuration is preferable in which the shaft support holes that are circular cross-section holes constituting the first bearing and the second bearing are provided in one member.

Also, from the viewpoint of ease in assembly and disassembly, it is preferable that the shaft member 36 and the link 54 are separate members as in the illustrated embodiments, but according to one embodiment, it is preferable that the operation wire is connected to a portion of the shaft member that protrudes radially outward, that is to say, the shaft member 36 and the link 54 are constituted as a single member, and the shaft member itself has the action point.

In the illustrated embodiments, the image sensor unit 30 and the air/water feeding tube 31 are arranged in the space formed to one side of the elevator 35, but according to one embodiment, it is preferable that other elements are arranged near the side of the elevator at the distal end of the insertion portion.

REFERENCE SIGNS LIST 10 ultrasonic endoscope
11 insertion portion
12 operation portion
15 distal end portion
16 bending portion
19 instrument insertion opening
23 ultrasonic probe
24 housing recession portion
24a first opposing wall
24b second opposing wall
24c step portion
24d third opposing wall
26 objective window 27 illumination window
28 air/water nozzle
30 image sensor unit
31 air/water feeding tube
32 instrument channel
35 elevator
35a support groove
35b narrow portion
35c shaft fitting hole
36 shaft member
36x axis
36a first non-circular cross-section portion
36b first circular cross-section portion
36c second non-circular cross-section portion
36d second circular cross-section portion
36e annular groove
40 main body
41 link housing space
41a first support wall
41b second support wall
42 shaft support hole
43 lid insertion space
43a small-diameter hole portion
43b large-diameter hole portion
44 O ring
45 link
45a shaft fitting hole
45b connection portion
46 operation wire
46a wire end portion
47 threaded passage hole
50 lid member
51 small diameter portion
52 large diameter portion
53 head portion
54 shaft support hole
55 fitting groove
55a bottom face
56 O ring
60, 160 fitting/holding member
60a flat face
61 plate-shaped portion
62 fitting recession portion
62a opposing face
62b connection face
63 base portion
64 coil support hole
64a coil abutting face
65 threaded hole
66 flange
67 fixing screw
68 stay coil
70 connection portion
71 covering member
75 pin insertion hole
75a inner circumferential surface
76 pin passage hole
76a countersink portion
77 fixing pin
77a shaft portion
77b conical surface

What is claimed is:

1. An endoscope including an elevator that is provided at a distal end of an insertion portion and changes a protruding direction of an instrument by swinging, and a drive member that swings the elevator according to an operation from an operation portion, the endoscope comprising:

a main body portion that has a housing recession portion that houses the elevator, a drive member arrangement space that houses the drive member and is liquid-tightly closed off from the housing recession portion, a lid insertion space that puts the drive member arrangement space and an outer space into communication, and a lid member that can be inserted into the lid insertion space and liquid-tightly closes off the lid insertion space when inserted; and a fitting/holding member that is fitted to the lid member inserted into the lid insertion space and is fixed to the main body portion by a mechanical fixing mechanism, the fitting/holding member restricting separation of the lid member from the lid insertion space, wherein:

the lid member has a protruding portion that protrudes from the lid insertion space into the drive member arrangement space, and the fitting/holding member can be inserted into the drive member arrangement space in a direction that is different from a protruding direction of the protruding portion of the lid member, the fitting/holding member being configured to be fitted to the protruding portion of the lid member when inserted.

2. The endoscope according to claim 1, wherein the protruding portion of the lid member has a substantially cylindrical outer circumferential surface, and includes a fitting groove that extends along a circumferential direction in the cylindrical outer circumferential surface, and the fitting/holding member includes a plate-shaped portion that is fitted to the fitting groove, the fitting/holding member being configured such that the plate-shaped portion abuts against an inner face that defines the drive member arrangement space and restricts movement of the lid member in a separation direction.

3. The endoscope according to claim 2, wherein the protruding portion of the lid member includes a pair of the fitting grooves that have bottom faces that are substantially parallel with each other, and the plate-shaped portion of the fitting/holding member includes a fitting recession portion having inner faces that sandwich the bottom faces of the pair of fitting grooves.

4. The endoscope according to claim 1, wherein in a state where the lid member is held in the insertion space via the fitting/holding member, an outer face of the lid member is substantially flush with an outer face of the main body portion that surrounds the lid member.

5. The endoscope according to claim 1, further comprising a shaft member that is configured to rotate about an axis, and that supports the elevator and is capable of rotating integrally with the elevator about the axis, wherein in a state where the lid member is held in the insertion space via the fitting/holding member, the lid member forms a bearing that supports the shaft member so as to be capable of rotating about the axis.

6. The endoscope according to claim 5, wherein the bearing is constituted by a circular cross-section portion provided at one end of the shaft member and a circular cross-section hole that is provided in the lid member, the circular cross-section portion being rotatably inserted into the circular cross-section hole.

7. The endoscope according to claim 5,
wherein the shaft member includes a non-circular cross-section portion at a different location from the circular cross-section portion in the direction along the axis, and
the drive member includes a non-circular cross-section hole into which the non-circular cross-section portion is fitted.

8. An endoscope comprising:
a main body portion that has a drive member arrangement space that houses a drive member that swings an elevator that is provided at a distal end of an insertion portion of the endoscope and changes a protruding direction of an instrument, a lid insertion space that puts the drive member arrangement space and an outer space surrounding the insertion portion into communication, and a lid member that can be inserted from the outside space into the lid insertion space, and liquid-tightly closes off the lid insertion space and closes off the drive member arrangement space from the outer space when inserted into the lid insertion space, the lid member being configured to have a protruding portion that protrudes from the lid insertion space into the drive member arrangement space; and
a fitting/holding member that is inserted into the drive member arrangement space, and is fixed inside the drive member arrangement space by sandwiching, along with the lid member, a wall between the drive member arrangement space and an outer space outside the main body portion and being fitted to the protruding portion of the lid member, thus restricting separation of the lid member from the lid insertion space.

9. The endoscope according to claim 8,
wherein the fitting/holding member can be inserted into the drive member arrangement space in a direction that transverses a protruding direction of the protruding portion of the lid member, the fitting/holding member being configured to be fitted to the protruding portion of the lid member when inserted.

10. An endoscope including an elevator that is provided at a distal end of an insertion portion and changes a protruding direction of an instrument by swinging, and a drive member that swings the elevator according to an operation from an operation portion, the endoscope comprising:
a main body portion that has a housing recession portion that houses the elevator, a drive member arrangement space that houses the drive member and is liquid-tightly closed off from the housing recession portion, a lid insertion space that puts the drive member arrangement space and an outer space into communication, and a lid member that can be inserted into the lid insertion space and liquid-tightly closes off the lid insertion space when inserted; and
a fitting/holding member that is fitted to the lid member inserted into the lid insertion space and is fixed to the main body portion by a mechanical fixing mechanism, the fitting/holding member restricting separation of the lid member from the lid insertion space,
wherein the drive member is connected by a wire to an operation mechanism provided in an operation portion of the endoscope, and a stay coil receives insertion of the wire and is arranged inside the insertion portion, and
the fitting/holding member has a coil support hole that receives insertion of one end of the stay coil.

11. An endoscope including an elevator that is provided at a distal end of an insertion portion and changes a protruding direction of an instrument by swinging, and a drive member that swings the elevator according to an operation from an operation portion, the endoscope comprising:
a main body portion that has a housing recession portion that houses the elevator, a drive member arrangement space that houses the drive member and is liquid-tightly closed off from the housing recession portion, a lid insertion space that puts the drive member arrangement space and an outer space into communication, and a lid member that can be inserted into the lid insertion space and liquid-tightly closes off the lid insertion space when inserted; and
a fitting/holding member that is fitted to the lid member inserted into the lid insertion space and is fixed to the main body portion by a mechanical fixing mechanism, the fitting/holding member restricting separation of the lid member from the lid insertion space,
wherein the lid insertion space is defined by a cylindrical inner circumferential surface, the lid member has a cylindrical outer circumferential surface that opposes the inner circumferential surface that defines the lid insertion space, and the endoscope further comprises an annular sealing member that liquid-tightly blocks a space between the inner circumferential surface that defines the lid insertion space and the outer circumferential surface of the lid member.

\* \* \* \* \*